United States Patent [19]

Byrne et al.

[11] Patent Number: 4,880,641
[45] Date of Patent: Nov. 14, 1989

[54] PINEAPPLE KETONE CARBONATE DERIVATIVES

[75] Inventors: Brian Byrne, Belleville, N.J.; Louise M. L. Lawter, Goshen, N.Y.

[73] Assignee: Hercules Incorporated, Wilmington, Del.

[21] Appl. No.: 192,058

[22] Filed: May 6, 1988

Related U.S. Application Data

[60] Division of Ser. No. 120,760, Nov. 9, 1987, Pat. No. 4,758,680, which is a continuation of Ser. No. 627,311, Jul. 2, 1984, abandoned.

[51] Int. Cl.[4] ............................................. A23L 1/235
[52] U.S. Cl. ........................................ 426/3; 426/536
[58] Field of Search ........................... 512/11; 424/49; 131/277; 426/536, 3

[56] References Cited

U.S. PATENT DOCUMENTS 4,758,680 7/1988 Byrne et al. ................. 426/536 X

Primary Examiner—Joseph Golian
Attorney, Agent, or Firm—Dale R. Lovercheck

[57] ABSTRACT

A compound of the general formula,

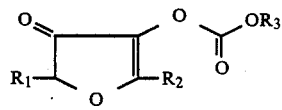

wherein $R_1$ and $R_2$ independently are —H, —CH$_3$, or —CH$_2$CH$_3$; and $R_3$ is alkyl of from 1 to 10 carbons or aryl of from 6 to 10 carbons.

2 Claims, No Drawings

PINEAPPLE KETONE CARBONATE DERIVATIVES

BACKGROUND OF THE INVENTION

This invention relates to flavors and specifically to modified pineapple ketone.

Pineapple ketone is the common name for the chemical 2,5-dimethyl-4-hydroxy-3(2H)-furanone. This is a compound found in pineapples, strawberries, raspberries, meats, and other foods. It has been found in cooked, roasted and fermented foods including coffee, roasted filbert, roasted almond and soy sauce. Pineapple ketone is known to be formed by the nonenzymatic browning process that occurs during roasting and baking.

Because of its cotton-candy, carmelized-sugar flavor, pineapple ketone is used extensively to compound synthetic flavors. Pineapple ketone reacts readily with amines, aldehydes and oxygen. In such cases, the pineapple ketone content of the flavors is reduced, lowering the effectiveness of the flavor.

When pineapple ketone is used in chewing-gum, it is quickly "washed out" by the chewing process, resulting in rapid loss of flavor. This "washing out" effect is due to pineapple ketone being water soluble.

Willhalm, et al., U.S. Pat. No. 3,455,702; Herman, et al., U.S. Pat. No. 3,697,291; and Demole, U.S. Pat. No. 3,983,885 disclose that flavor may be imparted to foodstuffs, beverages, meat, or tobacco by incorporating therein a minor proportion of a dihydrofuran.

Bruns, et al., U.S. Pat. No. 4,033,993; Grubbs, et al., U.S. Pat. 4,127,601; and Boden, et al, U.S. Pat. 4,397,789 each disclose carbonates used for their aroma.

SUMMARY OF THE INVENTION

A new pineapple ketone carbonate compound of the general formula,

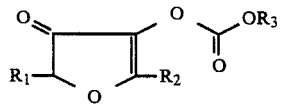

wherein $R_1$ and $R_2$ independently are —H, —CH$_3$, or —CH$_2$CH$_3$; and $R_3$ is alkyl of from 1 to 10 carbons or aryl of from 6 to 10 carbons.

The invention solves the wash out problems associated with the use of pineapple ketone, while extending the flavor over a longer period of time. By reacting pineapple ketone with an ethyl chloroformate or other alkyl chloroformates in triethylamine, the new and improved pineapple ketone carbonates are formed.

DETAILED DESCRIPTION OF THE INVENTION

The invention relates to new carbonates derived from pineapple ketone. By forming the new carbonate derivatives, the chemical reactivity of the resulting compounds is unexpectedly reduced compared with pineapple ketone; however, the flavor of the derivatives remains very similar to the flavor of pineapple ketone. This allows direct replacement of new carbonate derivatives in applications where pineapple ketone is normally used. Additionally, the increased oxidative stability of these derivatives over pineapple ketone allow their use in applications where pineapple ketone cannot be used or does not perform well. Such applications include but are not limited to perfumes, dry flavors and tobacco.

Furthermore, the new carbonate derivatives are not as water soluble as pineapple ketone, which allows these derivatives to be preferentially dissolved by chewing- or bubble-gum-base. This effect allows the derivatives to liberate pineapple ketone-like flavor slowly during the duration of the chew, creating a flavor prolongation effect.

The method of making new carbonates are novel because, although alcohols are known to react with ethyl chloroformate and other alkyl chloroformates to form alkyl carbonate derivatives, ketones or diones are not known to react with alkyl chloroformates to form carbonate derivatives.

An unexpected aspect of the invention is that the subject derivatives are more stable to oxidation than pineapple ketone. Hirvi, et al. [Lebensm.-Wiss. u.-Technol., 13, 324 (1980)] have indicated how sensitive pineapple ketone is to oxidation. At pH 4 it has a half-life of 120 days, while at pH 7 it has a half-life of 12 days. The increased oxidative stability of the subject carbonate derivatives over pineapple ketone is given in Example 3. An unexpected aspect of this invention is that the derivatives have a similar taste to pineapple ketone.

The invention offers the following advantages:
(a) The new carbonates have flavor properties similar to pineapple ketone;
(b) The new carbonates offer oxidative stabilities superior to pineapple ketone, allowing them to be used in situations where pineapple ketone will be unstable. Such situations include use as liquid flavors, and especially dry flavors;
(c) The new carbonates can be used in perfumes, whereas pineapple ketone is unstable leading to changes in the fragrance profile over time and discoloration of the formulation;
(d) The new carbonates prolong flavor in chewing-gum and bubble-gum.

Exemplary of the preferred extended flavor compounds and the invention are:

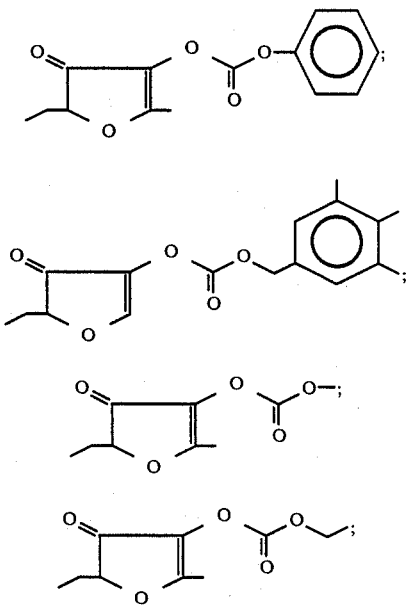

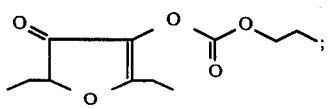

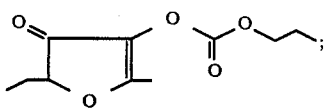

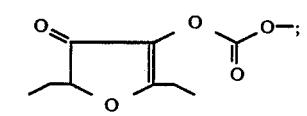

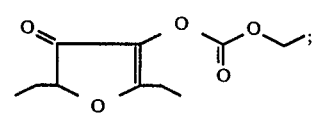

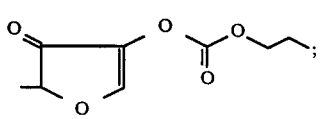

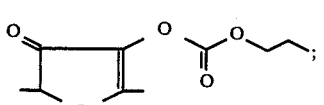

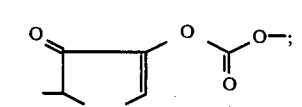

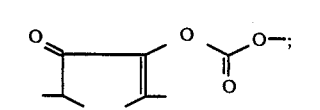

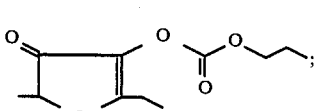

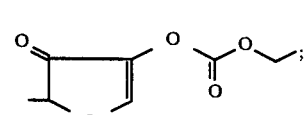

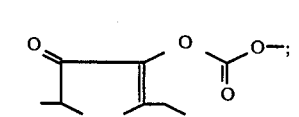

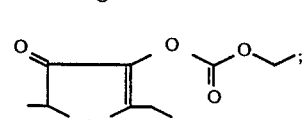

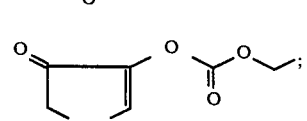

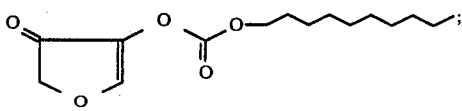

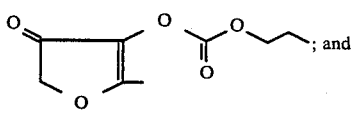

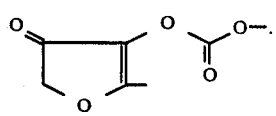

EXAMPLE 1

PREPARATION OF ETHYL 2,5-DIMETHYL-3-OXO-4(2H)-FURYL CARBONATE

A solution of 2,5-dimethyl-4-hydroxy-3(2H)-furanone (pineapple ketone, 133.0 g, 1.0 mole) and triethylamine (152.0 g, 1.5 moles) in methylene chloride (665 g) is cooled to 5° C. under nitrogen atmosphere. To the cooled solution is added over a period of 2.5 hours, a solution of ethyl chloroformate (127.7 g, 1.18 moles) in methylene chloride (600 g) stirred at 5°-8° C. for two additional hours. The reaction mixture is filtered through a Buchner funnel to remove the triethylamine hydrochloride. The salt is washed with methylene chloride (200 ml). The combined organic layers are washed twice with 100 ml portions of water and dried over sodium sulfate. The solvent is removed in vacuo and the crude product distilled (<0.1 torr) through a Goodloe column to yield 72.5% of ethyl 2,5-dimethyl-3-oxo-4(2H)-furyl carbonate product b.p. 87° C. (0.08 torr), IR (neat film) 2980(M), 1770(S), 1715(S), 1640(S), 1250(S) cm$^{-1}$, $^1$H NMR $\delta$1.58(t,J=8 Hz,3), 1.65 (d,J=7Hz,3), 2.32 (s,3), 4.45 (q,J=7Hz,2), 4.75 (q,J=7Hz,1), and 3.3% of the diadduct, diethyl 2,5-dimethyl-3,4-furyl dicarbonate, b.p. 110° C. (0.08 torr), IR (neat film 2980(M), 1770(S), 1250(S), $^1$H NMR $\delta$=1.50 (t,J=6 Hz,6) 2.3 (S,6) 4.45 (q,J=8 Hz,4).

EXAMPLE 2

PREPARATION OF METHYL 2,5-DIMETHYL-3-OXO-4(2H)-FURYL CARBONATE

A solution of 2,5-dimethyl-4-hydroxy-3(2H)-furanone (pineapple ketone, 44.0 g, 0.33 mole) and triethylamine (50.5 g, 0.5 mole) in methylene chloride (220 g) is cooled to 5° C. under nitrogen atmosphere. To the cooled solution is added over a period of 2.0 hours, a solution of methyl chloroformate (38.6 g, 0.41 mole) in methylene chloride (200 g), which is then stirred at 5°-8° C. for two additional hours. The reaction mixture is filtered through a Buchner funnel to remove the triethylamine hydrochloride. The salt is washed with methylene chloride (200 ml). The combined organic layers are washed twice with 100 ml portions of water and dried over sodium sulfate. The solvent is removed in vacuo and the crude product distilled (<0.1 torr) through a Goodloe column to yield 18 g of methyl 2,5-dimethyl-3-oxo-4(2H)-furyl carbonate product, b.p. 105° C.; IR (neat film) 2960(M), 1770(S), 1710(S), 1640(S), 1250(S), 1200(S) cm$^{-1}$; $^1$H NMR δ1.55(d, J=8 Hz,3), 2.28 (s,3), 3.95 (s,3), 4.70 (q, J=8 Hz,1).

EXAMPLE 3

OXIDATIVE STABILITY OF ETHYL 2,5-DIMETHYL-3-OXO-4(2H)-FURYL CARBONATE

Solutions containing respectively 10 percent carbonate and ten percent pineapple ketone in toluene are stirred in loosely capped vials at ambient temperature. Samples are taken periodically and the concentration of carbonate or ketone remaining determined by GLC (6'×⅛", 15% Carbowax-20M on 80/100 Chromasorb W, Helium=28 cc/min, 100°-210° at 8°/min). The experiment is repeated using ethanol as solvent. Results are shown below.

| COMPARATIVE STABILITY IN AIR (TOLUENE, AMBIENT TEMPERATURE) | | | |
|---|---|---|---|
| PINEAPPLE KETONE | | ETHYL CARBONATE OF EXAMPLE 1 | |
| Time (hours) | % Remaining | Time (hours) | % Remaining |
| 0 | 100 | 0 | 100 |
| 15 | 24 | 17 | 100 |
| 41 | 18 | 40 | 100 |
| 116 | 6 | 117 | 100 |
| 138 | 4 | 137 | 100 |
| 0 | 100 | 0 | 100 |
| 21 | 100 | 21 | 100 |
| 48 | 58 | 46 | 100 |
| 72 | 30 | 69 | 100 |
| 149 | 8 | 149 | 100 |
| 172 | 9 | 173 | 100 |

EXAMPLE 4

BUBBLE GUM

A typical bubble gum base is made with the following ingredients:

| | |
|---|---|
| Bubble Base T, Acid Balanced (L. A. Dreyfus Co., South Plainfield, NJ) | 135.00 parts |
| Corn syrup, 43° baume | 161.25 parts |
| Powdered sugar, confectioners 10X | 450.00 parts |
| Citric acid | 3.75 parts |
| Glycerine | 3.75 parts |
| Flavors | 7.50 parts |

All ingredients are mixed in a gum blender with a jacketed sidewall. To gum A is added 7.50 parts strawberry flavor 500389-U (Hercules, PFW Division, Middletown, N.Y.). To gum B is added 7.125 parts strawberry flavor 500389-U, plus 0.375 parts of ethyl carbonate pineapple ketone derivative from Example 1. The gums are cut into 5.0 grams pieces and evaluated by panelists. Both gums A and B have a long-lived strawberry flavor, with gum B having a higher overall rating for flavor prolongation after 10 minutes, as well as, having a higher and more sustained flavor intensity peak during the middle of the chew. Gum B has the best retained strawberry character throughout the chew.

Other features, advantages and specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What is claimed is:

1. A foodstuff composition comprising: a foodstuff and a flavor effective amount of a compound of the general formula,

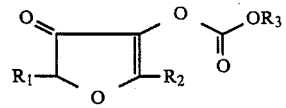

wherein $R_1$ and $R_2$ independently are —H, —CH$_3$ or —CH$_2$CH$_3$; and $R_3$ is alkyl of from 1 to 10 carbons are aryl of from 6 to 10 carbons.

2. A chewing gum composition comprising: chewing gum and a flavor effective amount of a compound of the general formula,

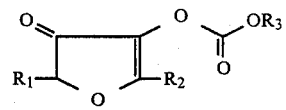

wherein $R_1$ and $R_2$ independently are —H, —CH$_3$ or —CH$_2$CH$_3$; and $R_3$ is alkyl of from 1 to 10 carbons or aryl of from 6 to 10 carbons.

* * * * *